(12) United States Patent
Paanasalo

(10) Patent No.: US 6,917,895 B2
(45) Date of Patent: Jul. 12, 2005

(54) METHOD FOR DETERMINATION OF ROLL DENSITY

(75) Inventor: Jari Paanasalo, Järvenpää (FI)

(73) Assignee: Metso Paper, Inc., Helsinki (FI)

( * ) Notice: Subject to any disclaimer, the term of this patent is extended or adjusted under 35 U.S.C. 154(b) by 0 days.

(21) Appl. No.: 10/480,331

(22) PCT Filed: May 30, 2002

(86) PCT No.: PCT/FI02/00464

§ 371 (c)(1),
(2), (4) Date: Dec. 11, 2003

(87) PCT Pub. No.: WO02/102693

PCT Pub. Date: Dec. 27, 2002

(65) Prior Publication Data

US 2004/0154391 A1 Aug. 12, 2004

(30) Foreign Application Priority Data

Jun. 15, 2001 (FI) .............................. 20011274

(51) Int. Cl.⁷ .............................................. G06F 15/00
(52) U.S. Cl. ...................................... 702/157; 702/155
(58) Field of Search ................................ 73/32 R, 159; 702/85, 97, 127, 137, 155, 157, 189, 190, 191; 242/412.2; 700/126

(56) References Cited

U.S. PATENT DOCUMENTS

| 3,898,436 | A | * | 8/1975 | Pottebaum et al. ............. 377/2 |
| 4,052,599 | A | * | 10/1977 | Whiteley et al. .............. 702/97 |
| 4,151,403 | A | * | 4/1979 | Woolston .................... 702/163 |
| 4,238,084 | A | * | 12/1980 | Kataoka ................... 242/413.1 |
| 4,335,439 | A | * | 6/1982 | St. Denis .................... 702/173 |
| 4,496,112 | A | * | 1/1985 | Olsson et al. ............. 242/413.1 |
| 4,508,284 | A | * | 4/1985 | Kataoka .................. 242/413.1 |
| 4,535,950 | A | * | 8/1985 | Lisnyansky ............... 242/534.2 |
| 4,576,344 | A | * | 3/1986 | Sasaki et al. ................ 242/547 |
| 4,594,880 | A | * | 6/1986 | Murdoch et al. ........... 73/32 R |
| 4,722,490 | A | * | 2/1988 | Doerfel .................... 242/412.2 |

(Continued)

FOREIGN PATENT DOCUMENTS

| DE | 4028322 C2 | * | 2/1993 |
| DE | 41 28 706 A1 | | 3/1993 |
| DE | 41 21 788 C2 | | 6/1993 |
| DE | 41 16 081 C2 | | 2/1995 |
| DE | 43 31 151 A1 | | 3/1995 |
| DE | 19533465 A1 | * | 3/1996 |
| DE | 195 23 885 A1 | | 1/1997 |
| DE | 198 19 276 A1 | | 11/1999 |
| DE | 198 21 318 A1 | | 11/1999 |
| DE | 199 00 737 A1 | | 7/2000 |
| DE | 199 31 217 A1 | | 1/2001 |
| EP | 0 397 594 A3 | | 5/1990 |
| WO | WO 93/15008 A1 | | 8/1993 |
| WO | WO 02/102693 A1 | | 12/2002 |

OTHER PUBLICATIONS

Haykin, S; Sayed, A; Zeidler, J; Yee, P; Wei, P; "Tracking of Linear Time–Variant Systems";Military Communications 95 IEEE Conference Record; vol. 2; Nov. 5–8, 1995; pp 602–606.*

(Continued)

*Primary Examiner*—Michael Nghiem
*Assistant Examiner*—Douglas N Washburn
(74) *Attorney, Agent, or Firm*—Stiennon & Stiennon

(57) ABSTRACT

A method for determining roll density in connection with a web reel. A known relation between the length (l), diameter (D), basis weight (b) and density (ρ) of the wound roll, formula (1) is used. Distortions caused in the measurement results by noise and other disturbances are eliminated by using a recursive time variant least squares method in the processing of the measurement results $l = \pi \rho (D^2 - D_0^2)/4b$.

11 Claims, 3 Drawing Sheets

U.S. PATENT DOCUMENTS

| | | | | |
|---|---|---|---|---|
| 5,023,820 A | * | 6/1991 | Baum | 702/163 |
| 5,039,023 A | * | 8/1991 | Hagens et al. | 242/547 |
| 5,265,460 A | | 11/1993 | Ellinger et al. | |
| 5,282,382 A | * | 2/1994 | Fiore et al. | 73/82 |
| 5,335,164 A | * | 8/1994 | Gough et al. | 700/29 |
| 5,390,536 A | | 2/1995 | Zhang et al. | |
| 5,394,322 A | * | 2/1995 | Hansen | 700/37 |
| 5,535,627 A | * | 7/1996 | Swanson et al. | 73/597 |
| 5,612,906 A | * | 3/1997 | Gotz | 702/94 |
| 5,687,077 A | * | 11/1997 | Gough, Jr. | 700/29 |
| 6,080,999 A | | 6/2000 | Mizuuchi | |
| 6,189,825 B1 | | 2/2001 | Mathieu et al. | |
| 6,209,817 B1 | | 4/2001 | Conrad et al. | |
| 6,363,297 B1 | * | 3/2002 | Wienholt et al. | 700/126 |
| 6,494,399 B1 | * | 12/2002 | Rautakorpi | 242/541.7 |

OTHER PUBLICATIONS

Chow, T; Gon Fei; Siu–Yeung Cho; "Higher Order Cumulants–Based Least Squares for Nonminimum–Phase Systems Identification"; IEEE Transactions on Industrial Electronics; vol. 44, issue 5; Oct. 1997; pp 707–716.*

Fechner, T; Neumerkel, D; Keller, I; "Adaptive Neural Network Filter for Steel Rolling"; IEEE World Congress on Computational Intelligence Neural Networks; vol. 6; Jun. 27–Jul. 2, 1994; pp 3915–3920.*

Kraus, F; "Stabilized Least Squares Estimators for Time–Variant Processes"; IEEE Proceedings of the 28th Conference on Decision and Control; Dec. 13, 1989; pp 1803–1804.*

Search Report issued in Finnish Patent App. No. 20011274.

International Search Report issued in PCT/FI02/00464.

International Preliminary Examination Report issued PCT/FI02/00464.

"The Measurement of Web Stresses During Roll Winding", David R. Roisum, Oklahoma State University, pp. 140–141, 1990.

"Nonlinear Model for Wound Roll Stress", Z. Hakiel, Tappi Journal, 1987.

"Contact Mechanical Model for Winding Nip" M. Jorkama, Teknillinen Korkeakoulu (University of Technology), 2001.

* cited by examiner

METHOD FOR DETERMINATION OF ROLL DENSITY

CROSS REFERENCES TO RELATED APPLICATIONS

This application is a U.S. National Stage application of International Application No. PCT/FI02/00464, filed May 30, 2002, and claims priority on Finnish Application No. 20011274, Filed Jun. 15, 2001, the disclosure of which is incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The invention concerns a method for determination of roll density, in which method the density of the web to be wound is determined in connection with the web reel and which method uses the known relation between the length, diameter, basis weight and density of the web to be wound $$l = \frac{\pi \rho (D^2 - D_0^2)}{4b},$$

l=length of web to be wound
$\pi = 3.1415926\ldots$
$\rho$=density
D=diameter
$D_o$=diameter of winding core
b=basis weight A calculation formula is known in the state of the art, which can be used e.g. to determine the ply thickness of the wound web or to measure the roll density.

The publication Roisum, D. R. "The Measurement of Web Stresses during Roll Winding", Oklahoma State University, 1990, s. 140–141 presents a formula in connection with measurement of roll density:

$$\rho = \frac{4b(length)}{\pi(d_i^2 - d_{i-1}^2)},$$

$\rho$=average web density over the measured distance
$\pi = 3.1415926\ldots$
length=cumulated web length over the measured distance
$d_i$=roll diameter on measurement occasion i
b=basis weight of web The formula was used in FI patent application 780893 for calculation of the thickness of a paper web:

$$d = \frac{R_k - R_{k-1}}{n_k - n_{k-1}}$$

$$d(L_k - L_{k-1}) = \pi(R_k^2 - R_{k-1}^2),$$

d=average web thickness over the measuring distance
$R_k$=roll radius on measurement occasion k
$L_k$=web length on measurement occasion k
$\pi = 3.1415926\ldots$
$n_k$=cumulative number of plies A similar formula is also presented in the publication Happonen, E. "Paperirullan Rullaustiheyden Mittauslaitteisto" ("Equipment for Measuring the Winding Density of a Paper Roll" Diploma Work), Diplomityö, Teknillinen Korkeakoulh (University of Technology), 1985 p. 17, which presents a calculation formula for the average thickness of wound paper in connection with the measurement of the thickness of wound paper over a certain winding distance $D_k = (R_k - R_{k-1})/(n_k - n_{k-1})$.

However, it has proved problematic in the determination of web density or thickness to eliminate the inexactness resulting in measurement results from noise and from other disturbances.

As is known in the state of the art, the formula has not been used generally, because the density measurement according to the formula has been prevented by the inexact diameter measurement and by the attending vibration frequency of the roll center. This is especially problematic when measurement of the location of the roll center is used in the diameter measurement.

As regards the state of the art, reference is also made to DE patent publication 41 28 706, which presents a method for determination of roll tightness when winding a material web on a winding machine, where the thickness of wound plies is found out for the roll tightness and wherein the length of the wound web affecting the diameter is measured directly. In the method, the roll diameter is measured directly by degrees as a transition of the roll center and then the ply thickness is calculated using a formula similar to the one described above $$S = \frac{(D_2^2 - D_1^2)\pi}{4\Delta l},$$

S=average web thickness over the measuring distance
$D_1$=roll diameter in the beginning of the measuring distance
$D_2$=roll diameter at the end of the measuring distance
$\pi = 3.1415926\ldots$
$\Delta l$=web length cumulated over the measuring distance In the calculation, high-frequency disturbances caused in the diameter measurement by vibration of the roll center are eliminated by low-pass filtration. In this known solution the filtration is thus based on the assumption that disturbances are of a high frequency and the filtration will thus be fairly rough.

The use of low-pass filtration to reduce the share of the noise of the measurement signal is based on the assumption that the noise summed on the measurement is of zero average value, that is, unbiased, and that its frequency content differs from the measurement signal proper. The filter removes from the measurement those higher frequencies, which the noise brings along, whereby the desired original measurement signal will remain. This may cause inexactness, since also a part of the desired measurement signal is filtered and also a part of the noise will remain. In addition, phase lag, that is, delay, may result in the measurement signal.

If low-pass filtration were to be used in order to achieve an efficient filtration at all machine ruling speeds and with all roll diameters, then the boundary frequency of low-pass filtration ought to be changed constantly as these factors are changing. Since the main reason for measurement noise is the waving in diameter measurement caused by the eccentricity of the roll center, the frequency content of measurement noise is strongly dependent on the rotation frequency of the roll, which again depends on the running speed and on the roll diameter, being typically at a maximum a little while after winding has begun. It is a problem with the state-of-the-art procedure that it is not easy in practice to implement a constant changing during operation of the boundary frequency of any higher rate low-pass filter.

Various ways of measuring the roll diameter are known in the state of the art, the most widely used being pulse measurement, wherein pulse measurement is used for measuring the roll circumference. The diameter information obtained through pulse measurement has been used in order to find out the web thickness. When one ply is completed on the roll, the length measure is taken-from the carrying roller and the paper thickness is obtained by finding out how quickly the roll diameter increases. It is problematic to determine the web thickness exactly, because when winding large-diameter rolls wherein the web is thin, differences in orders of magnitude have caused inexactness.

The roll hardness determines how tightly the roll is wound. This corresponds with a certain internal compression pressure distribution between the plies, which is the higher the tighter the roll. In addition, roll hardness depends on the hardness of the paper itself, that is, on the elastic modulus in the Z direction, which is different for different paper grades, that is, rolls of various kinds wound to the same tightness may have a different hardness. Roll density correlates with tightness or hardness, because an increased compression pressure will cause a deformation that will compress the paper layers together.

SUMMARY OF THE INVENTION

The invention aims at bringing about a method more exact than the density measuring methods known in the state of the art. A particular objective of the invention is to bring about a method, wherein distortions caused by noise and other disturbances in the measurement results are eliminated.

In order to achieve the objectives presented above and those emerging hereinafter the method according to the invention is mainly characterized in that in the method distortions caused by noise and by other disturbances in the measurement results are eliminated by using in the processing of measurement results a recursive time variant least squares method.

In the method according to the invention, a value is preferably determined for "filtration" based on measurement and mathematical statistics and calculus of probability are preferably applied, whereby an exact measurement results is attained, when that measurement noise is eliminated, which is mainly caused by oscillation of the roll center.

In an advantageous embodiment of the method for density measurement according to the invention, variables are initialized by two points determined by the nominal density before the first measurement. The correlation matrix and regression vector are then updated for each following measurement. The correlation matrix is then reversed, whereupon the paper thickness may be calculated. Based on the paper thickness the density is calculated and the error variance is updated, based on which the confidence limit is calculated, for example, for a 95% probability, and if the confidence limit is too big, the buffer length is increased, while if the confidence limit is too short the buffer length is decreased. The speed of oblivion is then determined and the following measurement is carried out after a chosen web length, for example, when the web length has increased by 1 meter.

The method according to the invention uses a recursive time variant least squares method, which is easy to implement in program terms and gives the density value directly and does not cause any distortions in the shape of the density curve. To the least squares method a method of mathematical statistics can be applied, with the aid of which a relation is obtained between exactness of measurement and the method's built-in filtration constant, whereby statistical confidence limits are determined for the measurement value, that is, the probability, by which the measurement value is closer to the correct value by a certain limit. In this manner any inaccuracies caused by noise and other disturbances in the measurement results are controlled in such a way that no distortions will occur in the measurement results.

Thus, the method according to the invention is based on a statistical method, which is not dependent on any frequency differentiation of signals, whereby filtration of measurement results is not performed in a separate stage, but if required the effect of filtration is estimated through the confidence limit, the value of which is directly related to the measurement signal proper. In accordance with an advantageous feature of the method according to the invention, the program itself determines a suitable filtration constant continuously based on the noise of the measurement.

In connection with the method according to the invention the diameter can be measured as a pulse measurement diameter in connection with winding-in, as a diameter measured from the location of the roll center, by a distance meter, for example, a laser meter or any other suitable measuring procedure that is sufficiently accurate. In unwinding, the location of the roll center does not change, so the diameter measurement is most suitably performed as a pulse measurement or using an ultrasonic distance meter from atop the roll.

In connection with the invention it is advantageous to use a linear sensor in measuring the tightness of winding-in separately for each station and based on the diameter and web length given by the linear sensor.

In the method according to the invention, the diameter may be measured in the desired manner, for example, by ultrasound, by a laser sensor, using which a measurement without contact is preferably achieved.

According to an advantageous feature of the method according to the invention, the determination of the measurement buffer length is also carried out automatically, whereby the measurement adapts to the varying noise and preserves its accuracy.

The method according to the invention thus utilizes a physical model in processing the measurement. When using a least squares procedure in this method according to the invention, this advantage is obtained, that is, an unbiased estimate of the density is obtained from the measurement data.

According to an advantageous additional feature of the method according to the invention, the measurement buffers are initialized in such a way that the measurement first shows the density value given by the user or the density value measured in the beginning of the previous winding, whence it begins following the measured value, as the roll starts rotating. This speeds up penetration of the initial transient and the measurement is made to begin as early as possible.

An even more exact initialization is achieved by first storing a suitable quantity of measurement data and by calculating the density backwards towards the smaller diameter from this data, whereby a very exact initial value is obtained for the roll bottom. However, this is tougher in terms of calculation.

In accordance with an advantageous application of the invention, the measuring method according to the invention may be extended further by applying an Extended time variant Kalman Filter. The purpose of the Kalman Filter is to utilize not only the direct measurement but also a known or estimated dynamic model of the system, which includes a physical description of the system known beforehand:

$$\dot{x}=f(x(t),u(t),t)+w(t)$$

$$z(t)=h(x(t),u(t),t)+v(t)$$

In this description x is the state vector, which defines the interior state of the system. In a winding model components of the state vector are e.g. the radial compression pressure and tangential tensile stress of the roll's surface ply. Vector u includes control magnitudes, such as e.g. the nip load, web tension, winding power, running speed. The control magnitudes are known or they can be measured directly. Vectors w and v are noises disturbing the system and the measurement. Vector z is a measurement magnitude, in this case the density. Function f is a description of the winding model, it tells how the roll's internal stress distribution results from the effect of the control magnitudes (for example, Jorkama, M. "*Contact Mechanical Model for Winding Nip*", *Teknillinen Korkeakouhlu*, 2001 and Hakiel, Z. "*Nonlinear Model for Wound Roll Strees*", *Tappi Journal*, 1987). The explicit time variable tells the effect on it by magnitudes not mentioned separately, such as e.g. the roll diameter and the paper thickness of the arriving web. Function h is a description of pressures through roll deformation on the density. It is dependent on the paper characteristics, such as the radial and tangential elastic modulus and the friction. The model may also be static, if dynamics are of no significance (slow changes of ratings):

$$x(t)=f(u(t),t)+w(t)$$

The idea of the Kalman filter is to form a reverse description $h^{-1}$, which is used to measure the roll pressure distribution indirectly, when the measured density and the dynamic physical model describing the winding are known. Forming the extended time variant Kalman filter is known in the art beginning from the system description. The model structure presented herein is by no means the only one that can be applied to winding, nor is the intention to be limited to it only.

The method according to the invention gives by little loading of the processor and light calculation and with easy implementation in a program such a result in an optimum manner in terms of mathematical statistics, which is very easy to set up for use with different paper grades.

BRIEF DESCRIPTION OF THE DRAWINGS

In the following, the invention will be described in greater detail with reference to the figures shown in the appended drawing, wherein.

DESCRIPTION OF THE PREFERRED EMBODIMENTS

Figure 1A:
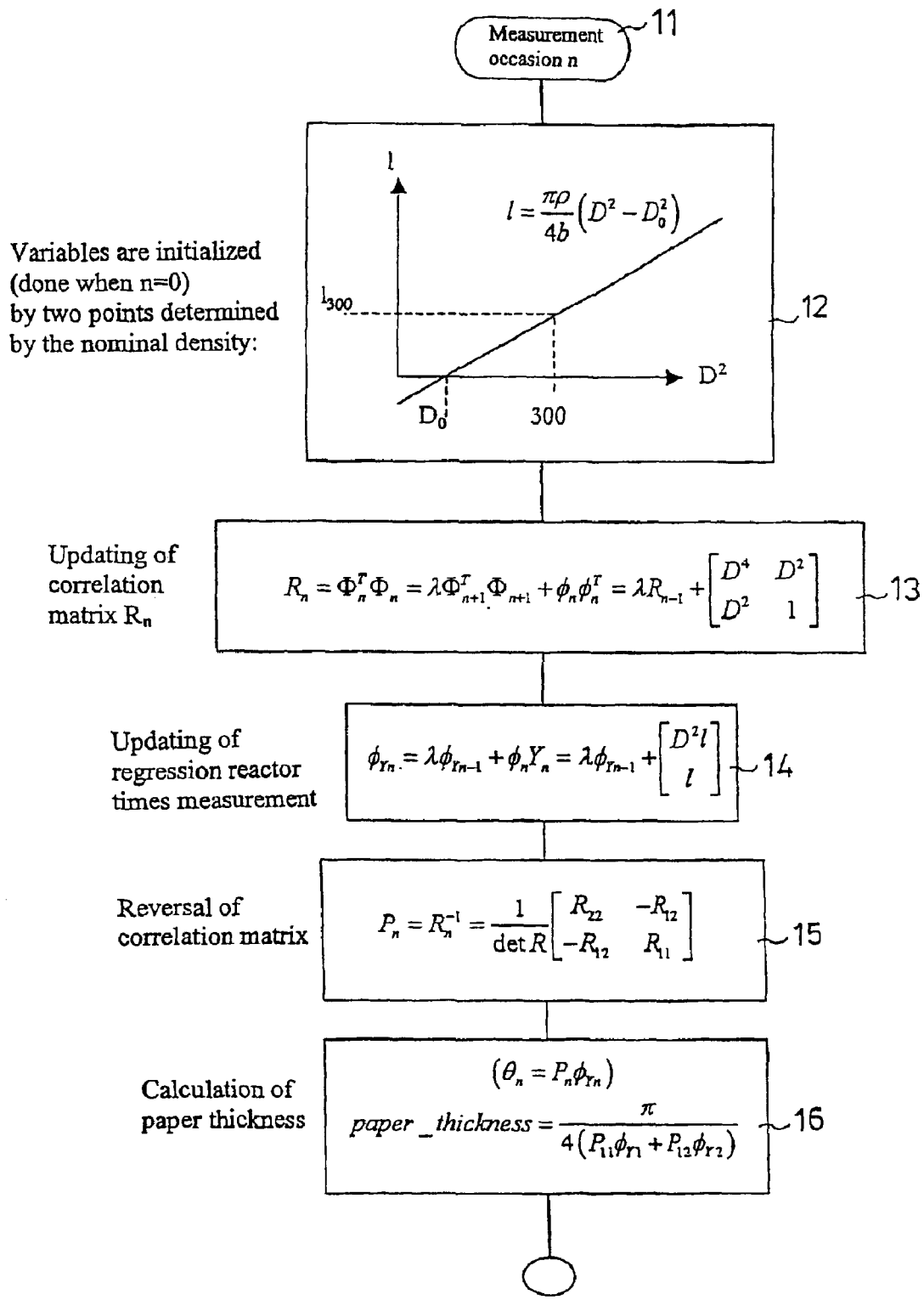
FIGS. 1A and 1B are schematic block views of the density measurement according to the invention.
Figure 1B:
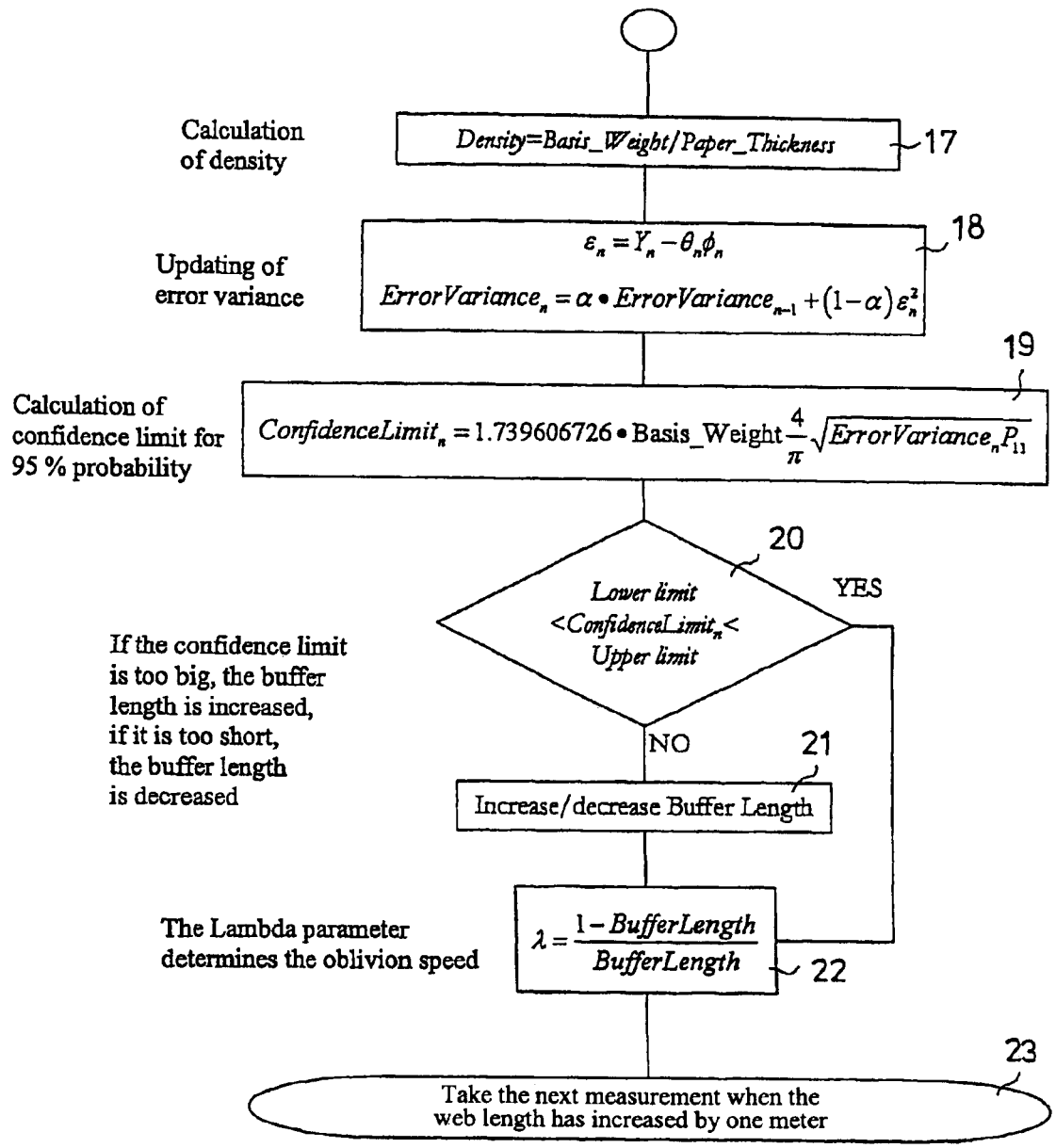

The variables shown in the formulas in FIGS. 1A and 1B have the following meanings:

$D_0$ = initial diameter
$D$ = measured roll diameter
$l$ = measured web length in roll
$b$ = basis weight given from screen
$\rho$ = nominal density given from screen
$\lambda$ = oblivion parameter (<1)
$\phi$ = regression vector = $[D^2 1]^T$
$Y$ = measurement = 1
$\theta$ = parameter vector, whose first component is inversely proportional to the paper thickness In the advantageous application of the density measurement method according to the invention shown in FIGS. 1A and 1B before the first measurement occasion, measurement occasions, block 11, the variables are initialized by two points determined by the nominal density, block 12, formula:

$$l = \frac{\pi\rho(D^2 - D_0^2)}{4b}$$

Thereafter, on each measurement occasion the correlation matrix and the regression vector are updated, blocks 13, 14, formulas:

$$R_n = \Phi_n^T \Phi_n = \lambda\Phi_{n+1}^T\Phi_{n+1} + \phi_n\phi_n^T = \lambda R_{n-1} + \begin{bmatrix} D^4 & D^2 \\ D^2 & 1 \end{bmatrix}$$

$$\phi_{Yn} = \lambda\phi_{Yn-1} + \phi_n Y_n = \lambda\phi_{Yn-1} + \begin{bmatrix} D^2 l \\ l \end{bmatrix}$$

Thereafter, the correlation matrix is reversed, whereupon the paper thickness can be calculated, blocks 15, 16, formulas:

$$P_n = R_n^{-1} = \frac{1}{detR}\begin{bmatrix} R_{22} & -R_{12} \\ -R_{12} & R_{11} \end{bmatrix}$$

$$(\theta_n = P_n \theta_{Yn})$$

$$\text{paper\_thickness} = \frac{\pi}{4(P_{11}\phi_{Y1} + P_{12}\phi_{Y2})}$$

Based on the paper thickness, the density is calculated, block 17, formula:

Density=Basis_Weight/Paper_Thickness and the error variance is updated, block 18, formula:

$$\epsilon_n = Y_n - \theta_n\phi_n$$

Error Variance$_n$=$\alpha\cdot$ErrorVariance$_{n-1}$+$(1-\alpha)\epsilon_n^2$ in which context the confidence limit is calculated, for example, for a probability of 95%, block 19, formula:

$$ConfidenceLimit_n = 1.739606726 \bullet$$

$$Basis\_Weight \frac{4}{\pi} \sqrt{ErrorVariance_n P_{11}}$$

and if the confidence limit is too large, the buffer length is increased, whereas if the confidence limit is too short, the buffer length is decreased, blocks 20, 21. Thereafter the speed of oblivion is determined, block 22, formula:

$$\lambda = \frac{1 - BufferLength}{BufferLength}$$

and the following measurement is performed after a chosen web length, for example, when the web length has increased by 1 meter, block 23.

Figure 2:
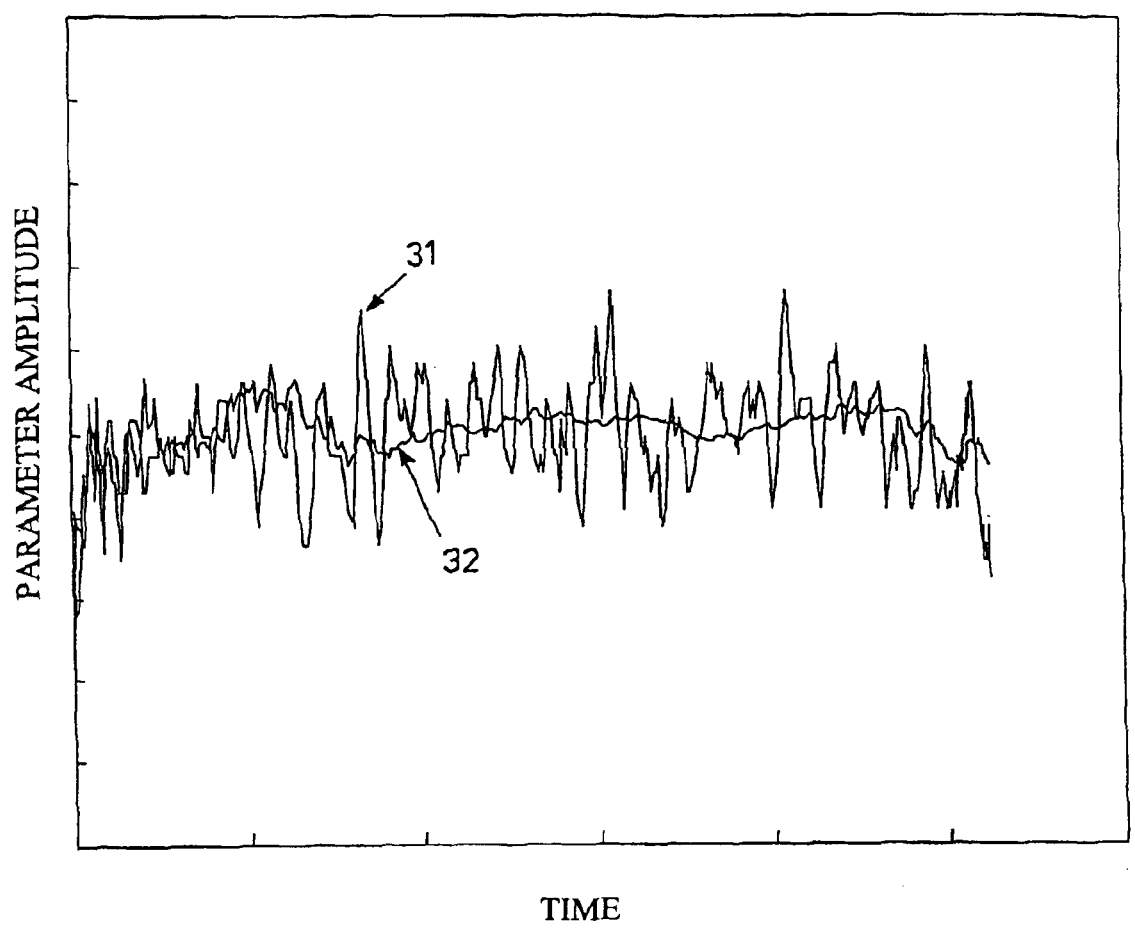
FIG. 2 is a schematic view of an example comparing the previously known pulse density measurement and the measuring method according to the invention.

FIG. 2 is a schematic view of an example comparing the previously known pulse density measurement and the measuring method according to the invention. In the figure, reference number 31 indicates the curve achieved with pulse density measurement and reference number 32 indicates the result curve achieved with the density measurement according to the method in accordance with the invention. As can be seen in FIG. 2, the method according to the invention, gives an exacter and more reliable result than the previously known density measurement method.

In the foregoing the invention was described by referring to its one advantageous application example only, but the intention is not to limit the intention in any way strictly to the details of that example.

What is claimed is:

1. In a method for determination of roll density, in which density of a wound roll formed of a web is determined at a multiplicity of occasions while reeling the web by measuring a parameter corresponding to at least one value selected from the group consisting of: measured web length in the roll (l), measured roll diameter (D), and basis weight of the web (b); and using a known relation between variables: measured web length in the roll (l), measured roll diameter (D), initial roll diameter($D_o$), basis weight of web (b) and density (ρ) of the wound roll;

$$l = \frac{\pi \rho (D^2 - D_0^2)}{4b}$$

the improvement comprising:
eliminating distortions in said measured parameter caused by noise and other disturbances, by using a recursive time variant least squares method in the processing of said measured parameter.

2. The method of claim 1 wherein a method of mathematical statistics is applied to the least squares method, whereby a relation is obtained between the at least one measured value exactness and the method's built-in elimination of noise and disturbances.

3. The method of claim 1 wherein statistical confidence limits are determined for the at least one measured value.

4. The method of claim 1, wherein before beginning a measurement occasion, initializing the at least one measured value by two points determined by a nominal density or by a preceding measurement; and further comprising carrying out the steps of:

updating a correlation matrix and a regression vector;

reversing the correlation matrix to calculate a paper thickness;

calculating density of the wound roll based on the paper thickness, followed by;

updating an error variance, followed by;

calculating a confidence limit for a selected probability;

if the confidence limit is below a selected lower limit or above a selected upper limit then changing a buffer length;

determining a speed of oblivion based on the buffer length; and beginning another measurement occasion after a selected web length has been wound or unwound from the wound roll.

5. The method of claim 1 wherein the recursive time variant least squares method uses an extended time variant Kalman filter for further processing of the measurement results and for measuring the internal stresses of the roll.

6. The method of claim 1 wherein the roll diameter is determined by contact-free measurement.

7. The method of claim 6 wherein the diameter is measured by pulse measurement, ultrasound or a laser sensor.

8. The method of claim 1 wherein the density is measured separately for each of a plurality of stations based on the roll diameter and web length given by a linear sensor.

9. The method of claim 1 wherein the method is applied in connection with winding-in of the web.

10. The method of claim 1 wherein the method is applied in connection with unwinding of the web.

11. The method of claim 1 wherein the method is applied in connection with winding of a paper or board web.

* * * * *